United States Patent [19]
Chapman et al.

[11] Patent Number: 6,156,894
[45] Date of Patent: Dec. 5, 2000

[54] PROCESS FOR MANUFACTURING α1L-ADRENOCEPTOR ANTAGONISTS

[75] Inventors: Robert Clark Chapman, Blythewood, S.C.; Jolyon Perkins, Kent, United Kingdom

[73] Assignee: Hoffman-La Roche Inc., Nutley, N.J.

[21] Appl. No.: 09/275,333

[22] Filed: Mar. 24, 1999

Related U.S. Application Data

[60] Provisional application No. 60/079,974, Mar. 30, 1998.

[51] Int. Cl.[7] .................... C07D 239/46; C07D 239/54
[52] U.S. Cl. ............................................. 544/310
[58] Field of Search ..................... 544/390, 310

[56] References Cited

U.S. PATENT DOCUMENTS

| | | | |
|---|---|---|---|
| 3,867,456 | 2/1975 | Kalopissis et al. | 260/574 |
| 3,971,784 | 7/1976 | Tada | 544/310 |
| 5,859,014 | 1/1999 | Bantle et al. | 544/295 |

FOREIGN PATENT DOCUMENTS

| | | |
|---|---|---|
| 0 748 800 A2 | 5/1996 | European Pat. Off. . |
| 0 748 800 | 12/1996 | European Pat. Off. . |
| 0877022 | 11/1998 | European Pat. Off. . |
| 50-88078 | 7/1975 | Japan . |
| 9-100269 | 4/1997 | Japan . |
| 1 487 335 | 9/1977 | United Kingdom . |

OTHER PUBLICATIONS

Greene, T. W., Protective Group in Organic Synthesis, pp. 284–287, 1981.

Marturisyan et al. Izv.Akad. Nauk SSSR, Ser. Khim. 5, 1127–31, 1970.

Martirosyan et al. Izv.Akad. Nauk SSSR, Ser. Khim. 8, 184–4, 1970.

Chem. Abstract, vol. 73, No. 13, No. 66534r, 1970.

Chem. Abstract, vol. 74, No. 33, No. 54134t, 1970.

Kasnar, B.; et al., Nucleosides & Nucleotides, 16, pp. 1067–1071 (1997).

*Primary Examiner*—Mukund J. Shah
*Assistant Examiner*—V Balasubramanian
*Attorney, Agent, or Firm*—George W. Johnston; William H. Epstein; John P. Parise

[57] ABSTRACT

A process is useful for making compounds of the formula:

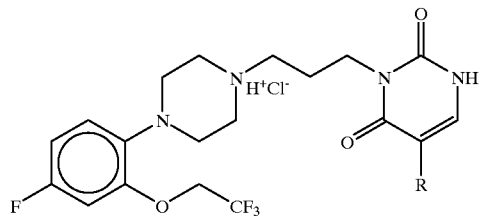

wherein R is hydro, methyl, or fluoro.

Valuable intermediates in this process include:

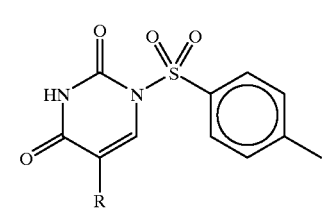

and

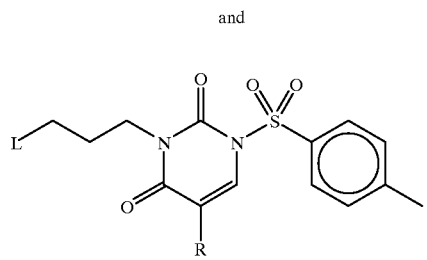

wherein R is hydro, methyl, or fluoro, and L is a leaving group.

9 Claims, No Drawings

PROCESS FOR MANUFACTURING α1L-ADRENOCEPTOR ANTAGONISTS

This application claims benefit of Provisional Application No. 60/079,974, filed Mar. 30, 1998.

BACKGROUND OF THE INVENTION

1. Field

The invention relates to a method for producing $\alpha_{1L}$-adrenoceptor antagonists and to intermediates involved in this process.

2. Description

The $\alpha_{1L}$-adrenoceptor antagonist having the formula:

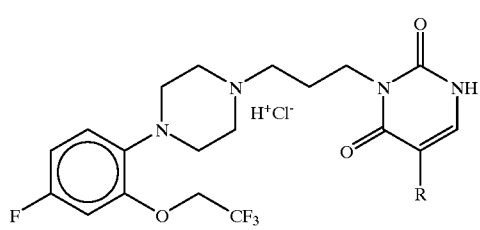

I wherein R is hydro, methyl, or fluoro, is beneficial in the treatment of benign prostatic hyperplasia. $\alpha_{1L}$-Adrenoceptorantagonists as a group are known to selectively reduce $\alpha_{1L}$-adrenoceptor hyperactivity in prostatic and/or lower urinary tract smooth muscle, without significantly affecting blood pressure or causing postural hypotension. Compounds encompassing the compound of Formula, I and a method for their manufacture, are described in European Patent Publication No. 0 748 800, published Dec. 18, 1996. The present invention provides an economical alternative process for manufacturing this $\alpha_{1L}$-adrenoceptor antagonist.

SUMMARY OF THE INVENTION

The subject invention provides compounds of the formulas:

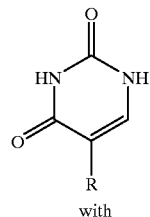

IV wherein R is hydro, methyl, or fluoro; and

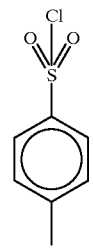

V wherein R is hydro, methyl, or fluoro, and L is a leaving group.

The subject invention also provides a process for producing a compound of the formula:

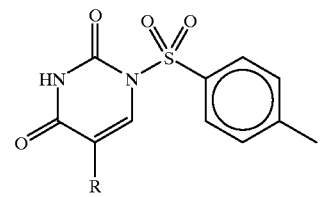

IV wherein R is hydro, methyl, or fluoro, which comprises reacting

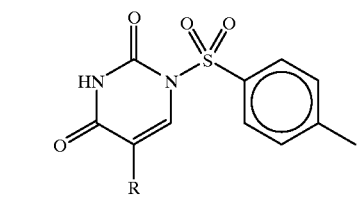

II with

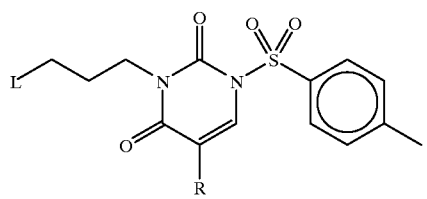

III wherein R is hydro, methyl, or fluoro, under basic conditions to produce the compound of formula IV.

The subject invention further provides a process for producing a compound of the formula:

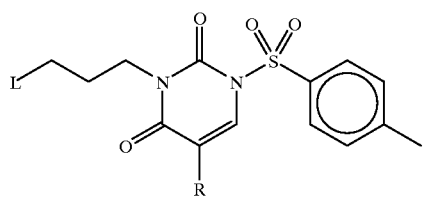

V wherein R is hydro, methyl, or fluoro, which comprises reacting

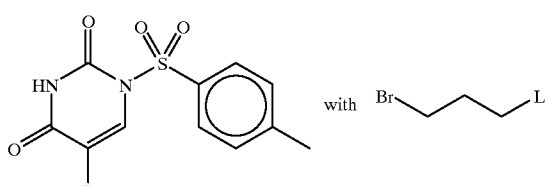

IV wherein R is hydro, methyl, or fluoro, wherein L is a leaving group, under basic conditions to produce the compound of formula V.

Moreover, the subject invention provides a process for producing a compound of the formula:

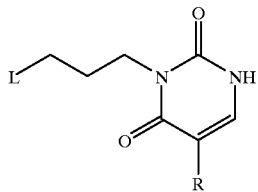

VI wherein R is hydro, methyl, or fluoro, and L is leaving group, which comprises cleaving the tosyl group from the compound of the formula:

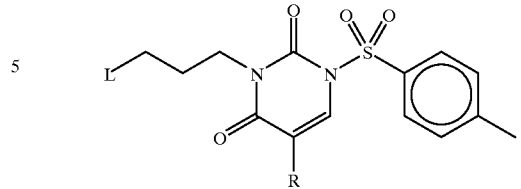

V wherein R is hydro, methyl, or fluoro, and L is leaving group, in the presence of a cleaving agent to produce the compound of formula VI.

DETAILED DESCRIPTION OF THE INVENTION

The subject invention will now be described in terms of its preferred embodiments. These embodiments are set forth to aid in understanding the invention but are not to be construed as limiting.

The following scheme illustrates a preferred embodiment of the subject process for preparing the compound of Formula I. Steps 1–3 represent novel aspects of the subject invention. Steps 4 and 5 have previously been described in European Patent Publication No. 0 748 800.

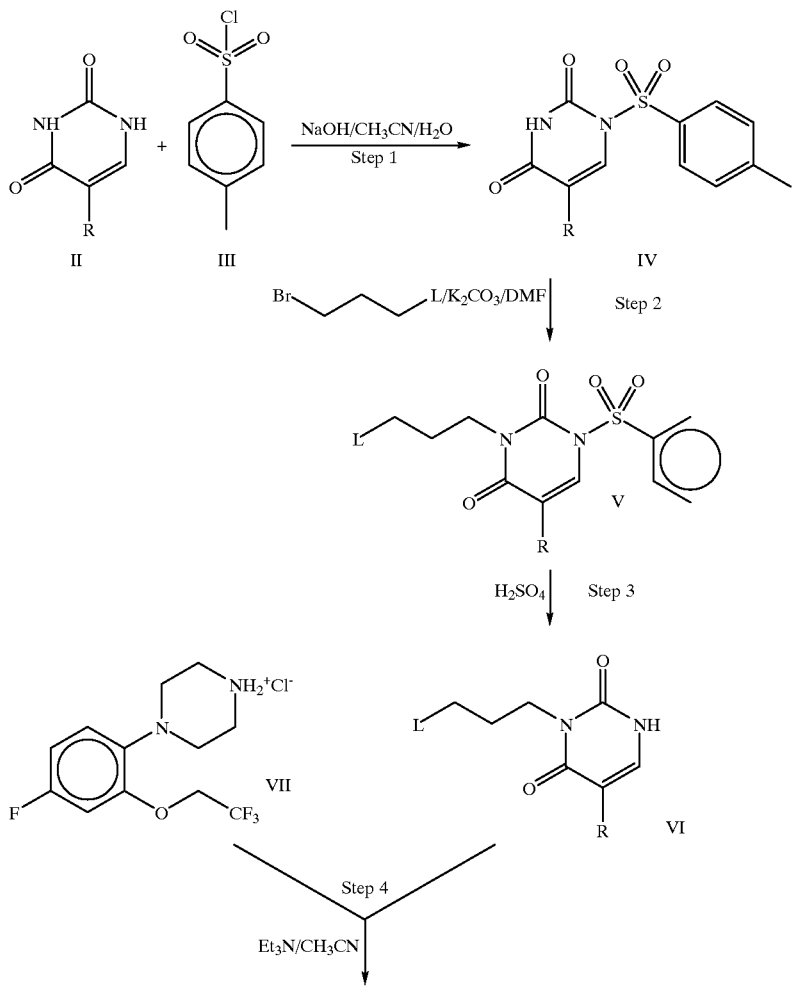

-continued

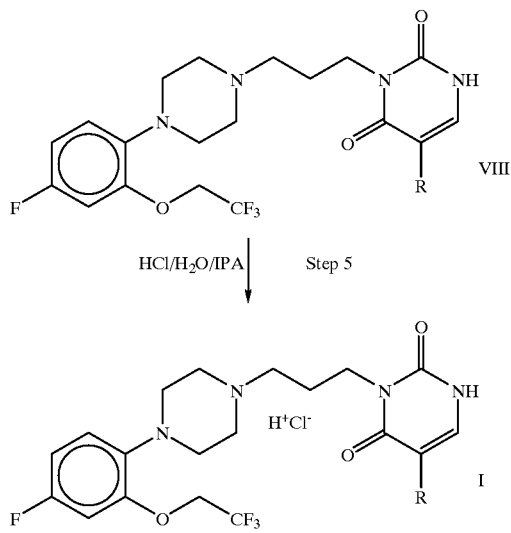

The compounds of Formulas II, III and VII are readily obtainable and/or preparable by methods known in the art.

Step One

The first step in the subject process involves reacting the compound of Formula II (uracil, when R is hydro; thymine, when R is methyl; or 5-fluorouracil when R is fluorine) with tosyl chloride (Formula III) to form the compound of Formula IV as follows:

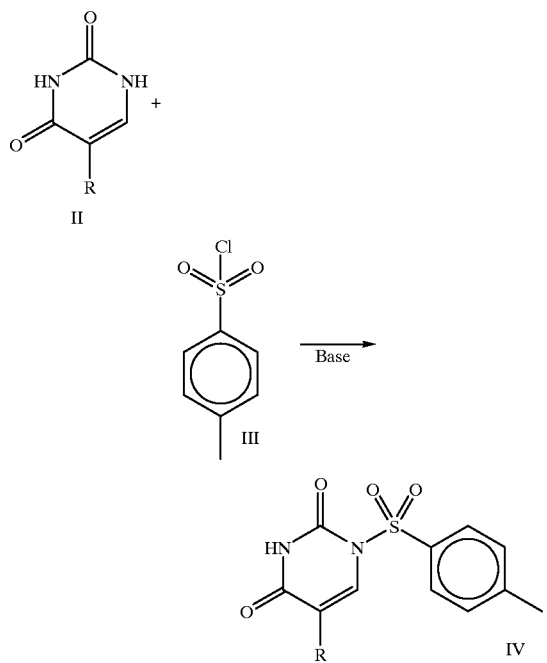

The base used in the first step is preferably NaOH. However, other bases such as $K_2CO_3$ and $Et_3N$ can also be used. The reaction is typically performed in a solvent comprising $CH_3CN/H_2O$. However, other solvents such as N-methylpyrolidinone ("NMP"), acetone, N,N-dimethylformamide ("DMF"), tetrahydrofuran ("THF"), sulfolane, 1,3-dimethyl-2-imidazolidinone ("DMI"), taken alone or in combination with water, can be used. A temperature range of from about 15° C. to about 25° C. using sodium hydroxide in acetonitrile/water is preferred, although a much wider temperature range can be utilized. For example, a temperature range of from about −10° to about 80° C. is operable. To obtain optimal product recovery, the reaction mixture should be acidified to a pH less than 8.0 following the treatment.

Step Two

The second step involves reacting the compound of Formula IV with 1-L-3-bromopropane, (L is a leaving group) under basic conditions to form the compound of Formula V as follows:

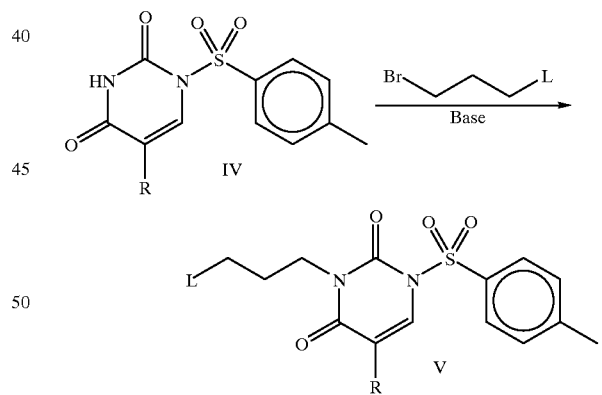

L is a leaving group and has the meaning conventionally associated with the term "leaving group" in synthetic organic chemistry, that is, an atom or group that is displaceable under alkylating conditions. The term "leaving group" includes halogen, for example chlorine and bromide; alkanesulfonyloxys, for example methanesulfonyloxy and ethanesulfonyloxy; arenesulfonyloxys, for example benzylsulfonyloxy and tosyloxy; thienyloxy; dihalophosphinoyloxy; tetrahalophosphaoxy; and the like. The leaving group should be selected so as to be chemically less reactive (except of course when the leaving group is bromine wherein it will be equally reactive) than the reacting group, bromine, to ensure proper reaction.

The base used in the second step is preferably $K_2CO_3$. However, other bases can be used. The selection of an appropriate base is within the skill of an artisan who has read the present specification. However, for guidance, a poor nucleophile should be selected, such as triethylamine, trimethylamine, Hunig's base or other tertiary amine.

Reacting is typically performed in a solvent comprising DMF. Preferred conditions involve cooling the reaction mixture containing the compound of Formula IV wherein R is methyl (1-tosylthymine), anhydrous potassium carbonate and DMF to −40 to 70° C., preferably −10 to 10° C., most preferably 0 to 5° C. followed by rapid addition of 1-bromo-3-chloropropane. The reaction mixture is then stirred at −40 to 70° C., preferably −5 to 15° C., most preferably 5±5° C., for 2–20 hours, preferably 3–7 hours, and most preferably 5 hours. After this stirring, the temperature is gradually increased over a 6 hour period to 5 to 25° C., preferably 15±5° C. The reaction mixture temperature is then raised to 50±5° C. and diluted with deionized water to precipitate the product. Other solvents, such as NMP, acetone, DMF, THF, sulfolane, and DMI, alone or in combination with water, can be used.

Step Three

The third step involves cleaving the tosyl group in the presence of a cleaving agent as follows:

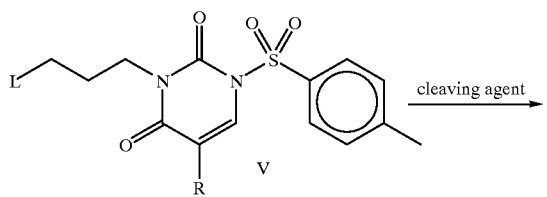

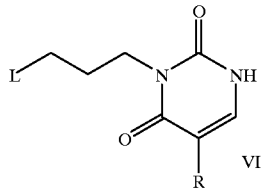

The cleaving agent in the third step may be an acid, basic or nucleophilic agent, including sodium methoxide or ethoxide, concentrated HCl, anhydrous HF, or most preferably concentrated sulfuric acid. The reaction temperature should be between −20 and 130° C., preferably between −5 and 80° C., most preferably 0±5° C. during the combination of the two components. The temperature should be kept at 45±5° C. during the balance of the reaction.

The following examples were actually performed.

Example 1

To a mechanically stirred solution of 200.0 g thymine (1.586 mol) in a mixture of 1.33 l water and 65 g sodium hydroxide (1.6 mol) under nitrogen atmosphere were added simultaneously a solution of 378.1 g p-toluenesulphonyl chloride (1.98 mol) in 1.0 l acetonitrile over 60 min and a solution of 95.16 g NaOH (2.38 mol) in 0.330 l water added over 65 min while cooling the reaction in a water bath from an initial temperature of 40° C. to about 35° C. The reaction was stirred an additional 50 min following completion of the additions, and then cooled to 0–5° C. The reaction mixture was then acidified by adding 242 g conc. HCl (2.45 mol) over 10 min. The reaction mixture was stirred an additional 20 min at 0–5° C. followed by vacuum filtration. The solid was vacuum dried at 55° C. overnight. 433.1 g 1-tosylthymine (97% yield, white crystals) was obtained.

Example 2

To a mechanically stirred solution of 0.34 kg 1-tosylthymine (2.70 mol) (produced by the process of Example 1) in 1.0 l dimethylformamide under nitrogen atmosphere at ambient temperature was added 0.240 kg 1-bromo-3-chloropropane (28.8 mmol) followed by 0.235 kg potassium carbonate (29.9 mmol) powder (−325 mesh) and an additional 0.38 l dimethylformamide. The reaction mixture warmed to 31° C. due to an exotherm and was subsequently heated to 50° C. The resultant suspension was stirred for 2.5 hr at 50° C. The reaction mixture was then added slowly with stirring top 4.5 l cold water. The original reaction vessel was rinsed into the second vessel with an additional 1.7 l cold water. The mixture was cooled to 0–5° C. and stirred at this temperature for 30 min to precipitate the product. The product was vacuum filtered, the filtrate was washed with 1.0 l cold water followed by 1.0 l heptane. The product was vacuum dried at 50° C. overnight yielding 0.414 kg 3-(3-chloropropyl)-1-tosylthymine (96% yield of fine white crystals).

Example 3

To a 1 l jacketed resin flask ("Reactor 1") was added under nitrogen atmosphere 0.395 kg (3-3-chloropropyl)-1-tosylthymine (1.11 mol) (produced by the process of Example 2) followed by addition at ambient temperature of 0.492 l concentrated sulfuric acid. An exotherm to 45° C. was observed. The flask was maintained at 45° C. for 1 hr while 3.0 l water was added to a second vessel ("Reactor 2") and cooled to 0–5° C. with −5° C. on the jacket. The reaction mixture in Reactor 1 was slowly metered into Reactor 2 which was agitated with −5° C. jacket temperature over 35 min. The pot temperature rose to 25° C. 1.0 l water was used to rinse the residual contents of Reactor 1 into Reactor 2. Reactor 2 was cooled to 3° C. and the contents was vacuum filtered. The solid was washed with 3×4 l cold water and dried in a vacuum oven overnight at 50° C. 0.204 kg 3-(3-chloropropyl)-1-tosylthymine (1.01 mol, 90.9% yield), a white crystalline solid was obtained.

The subject invention has been described in terms of its preferred embodiments. Upon reading the specification, other variant embodiments will become obvious to the skilled artisan. These variations are to be considered within the scope and spirit of the invention which should only be limited by the claims that follow and their equivalents.

What is claimed is:

1. A process for producing a compound of the formula:

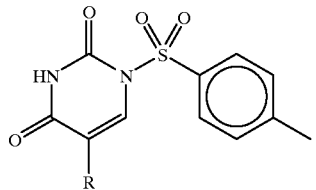

IV wherein R is hydro, methyl, or fluoro, which comprises reacting:

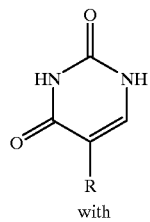

II with

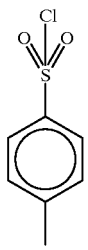

III wherein R is as above,
in the presence of NaOH in an acetonitrile/water solvent at a temperature in the range of from about 15° C. to about 25° C., to produce the compound of Formula IV.

2. A process for producing a compound of the formula:

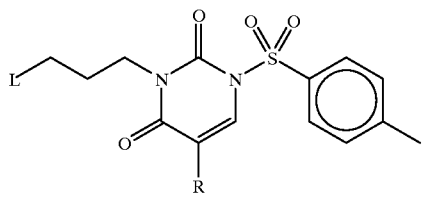

V wherein R is hydro, methyl, or fluoro, and L is halogen, which comprises reacting

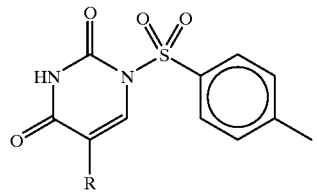

IV wherein R and L are as above, in the presence of $K_2CO_3$ in N,N-dimethylformamide at a temperature in the range of from about −40° C. to about 70° C. to produce the compound of Formula V.

3. The process of claim 1, wherein the reacting is performed at a temperature in the range of about 50° C.

4. A process for producing a compound of the formula:

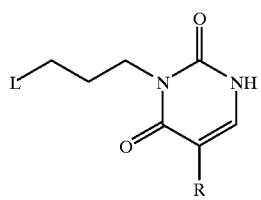

VI wherein R is hydro, methyl, or fluoro, and L is halogen, which comprises cleaving the tosyl group from the compound of the formula

V (structure shown)

wherein R and L are as above, in the presence of a $H_2SO_4$ to produce the compound of Formula VI.

5. The process of claim 4, wherein the reacting is performed at a temperature in the range of from about −20° C. to about 130° C.

6. The process of claim 5, wherein the reacting is performed at a temperature in the range of from about −5° C. to about 80° C.

7. The process of claim 6, wherein the reacting is performed at a temperature of about 5±5° C.

8. The process of claim 7, wherein the temperature is about 45±5° C.

9. A compound of the formula:

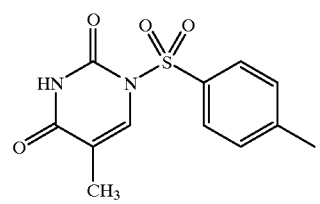

* * * * *

UNITED STATES PATENT AND TRADEMARK OFFICE
CERTIFICATE OF CORRECTION

PATENT NO.    : 6,156,894
DATED         : December 5, 2000
INVENTOR(S)   : Robert Clark Chapman and Jolyon Perkins It is certified that error appears in the above-identified patent and that said Letters Patent is hereby corrected as shown below:

Column 10,
Line 4, delete "claim 1," and insert -- claim 2, --.

Signed and Sealed this

Twenty-fourth Day of September, 2002

Attest:

JAMES E. ROGAN
Attesting Officer      Director of the United States Patent and Trademark Office